(12) United States Patent
Ogino et al.

(10) Patent No.: US 8,604,685 B2
(45) Date of Patent: Dec. 10, 2013

(54) ELECTRIC DISCHARGE TUBE, METHOD FOR FORMING REFLECTIVE FILM OF ELECTRIC DISCHARGE TUBE, AND LIGHT EMITTING DEVICE

(75) Inventors: Yasushi Ogino, Kyoto (JP); Kiyoshi Tsutsumi, Hyogo (JP); Toshiaki Murai, Osaka (JP)

(73) Assignee: Panasonic Corporation, Osaka (JP)

( * ) Notice: Subject to any disclaimer, the term of this patent is extended or adjusted under 35 U.S.C. 154(b) by 182 days.

(21) Appl. No.: 13/145,458

(22) PCT Filed: Jan. 25, 2010

(86) PCT No.: PCT/JP2010/000384
§ 371 (c)(1),
(2), (4) Date: Jul. 20, 2011

(87) PCT Pub. No.: WO2010/084770
PCT Pub. Date: Jul. 29, 2010

(65) Prior Publication Data
US 2012/0019119 A1    Jan. 26, 2012

(30) Foreign Application Priority Data
Jan. 26, 2009  (JP) ................ 2009-014017

(51) Int. Cl.
*H01J 61/35* (2006.01)
(52) U.S. Cl.
USPC ............. 313/488; 313/489; 313/113; 445/11
(58) Field of Classification Search
USPC ......... 313/488, 489, 113; 445/9–11; 362/260, 362/321, 327, 347, 354
See application file for complete search history.

(56) References Cited

U.S. PATENT DOCUMENTS

| | | | |
|---|---|---|---|
| 5,702,179 A | 12/1997 | Sidwell et al. | |
| 6,333,509 B1 | 12/2001 | Lumpp | |
| 6,384,526 B1 | 5/2002 | Peters | |
| 2005/0024880 A1* | 2/2005 | Moench et al. | 362/342 |
| 2005/0066901 A1* | 3/2005 | Isoda | 118/726 |
| 2006/0071590 A1* | 4/2006 | Martin et al. | 313/488 |

FOREIGN PATENT DOCUMENTS

| | | |
|---|---|---|
| JP | 60-109261 U | 7/1985 |
| JP | 4-27562 U | 3/1992 |
| JP | 4-206252 A | 7/1992 |
| JP | 6-29002 A | 2/1994 |
| JP | 7-72535 A | 3/1995 |
| JP | 09-180683 A | 7/1997 |
| JP | 9-180683 A | 7/1997 |
| JP | 2000-514592 A | 10/2000 |
| JP | 2006-196347 A | 7/2006 |
| WO | WO 98/01700 A3 | 1/1998 |

OTHER PUBLICATIONS

International Search Report for PCT/JP2010/000384, Mar. 9, 2010.
Supplementary European Search Report for Application No. EP 10733377, dated Jan. 15, 2013.

* cited by examiner

*Primary Examiner* — Karabi Guharay
(74) *Attorney, Agent, or Firm* — RatnerPrestia (57) ABSTRACT

A light emitting device includes a glass bulb and a reflective film formed in a region having an angle of at least 230° on an outer peripheral surface of the glass bulb. The light emitting device can obtain the reflective film having a sufficient film thickness in a wide region on an outer peripheral surface of an electric discharge tube and has a uniform light intensity distribution.

11 Claims, 10 Drawing Sheets

| REFLECTIVE FILM THICKNESS | 10nm | 20nm | 30nm | 40nm | 50nm |
|---|---|---|---|---|---|
| REFLECTANCE (%) | 37.24 | 61.09 | 77.48 | 85.90 | 91.81 |
| REFLECTIVE FILM THICKNESS | 60nm | 70nm | 80nm | 90nm | 100nm |
| REFLECTANCE (%) | 94.36 | 95.66 | 96.31 | 96.64 | 96.81 |
| REFLECTIVE FILM THICKNESS | 110nm | 120nm | 130nm | 140nm | 150nm |
| REFLECTANCE (%) | 96.92 | 96.98 | 96.98 | 96.98 | 96.98 |
| REFLECTIVE FILM THICKNESS | 160nm | 170nm | 180nm | 190nm | 200nm |
| REFLECTANCE (%) | 96.98 | 96.98 | 96.98 | 96.98 | 96.98 |

| DEPOSITION ANGLE | OUTER DIAMETER (mm) | OUTER RADIUS Ro(mm) | INTERNAL DIAMETER (mm) | INTERNAL RADIUS Ri(mm) | ANGLE OF APERTURE (°) | DEPOSITION ANGLE (°) |
|---|---|---|---|---|---|---|
| ELECTRIC DISCHARGE TUBE OUTER DIAMETER | 3.5 | 1.75 | 2.3 | 1.15 | 97.8 | 262.2 |
| | 3.1 | 1.55 | 1.75 | 0.875 | 111.3 | 248.7 |
| | 2.5 | 1.25 | 1.5 | 0.75 | 106.3 | 253.7 |
| | 2 | 1 | 1.5 | 0.75 | 82.8 | 277.2 |
| | 2 | 1 | 1.3 | 0.65 | 98.9 | 261.1 |
| | 2 | 1 | 1 | 0.5 | 120.0 | 240.0 |
| | 1.8 | 0.9 | 1 | 0.5 | 112.5 | 247.5 |
| | 1.5 | 0.75 | 1 | 0.5 | 96.4 | 263.6 |
| | 1.3 | 0.65 | 0.85 | 0.425 | 98.3 | 261.7 |

FIG. 5B

| DEPOSITION ANGLE | OUTER DIAMETER (mm) | OUTER RADIUS Ro(mm) | INTERNAL DIAMETER (mm) | INTERNAL RADIUS Ri(mm) | ANGLE OF APERTURE (°) | DEPOSITION ANGLE (°) |
|---|---|---|---|---|---|---|
| ELECTRIC DISCHARGE TUBE OUTER DIAMETER | 1.1 | 0.55 | 0.5 | 0.25 | 125.9 | 234.1 |
| | 3.6 | 1.8 | 2.8 | 1.4 | 77.9 | 282.1 |
| | 4 | 2 | 3.3 | 1.65 | 68.8 | 291.2 |

| OUTER DIAMETER | PROTECTIVE FILM ABSENCE· REFLECTIVE FILM ABSENCE | PROTECTIVE FILM PRESENCE· REFLECTIVE FILM ABSENCE | PROTECTIVE FILM ABSENCE· REFLECTIVE FILM PRESENCE | PROTECTIVE FILM PRESENCE· REFLECTIVE FILM PRESENCE |
|---|---|---|---|---|
| 1.3mm | 6420 K | 6230 K | 6370 K | 6050 K |
| 1.8mm | 6620 K | 6410 K | 6510 K | 6210 K |

ELECTRIC DISCHARGE TUBE, METHOD FOR FORMING REFLECTIVE FILM OF ELECTRIC DISCHARGE TUBE, AND LIGHT EMITTING DEVICE

This application is a U.S. National Phase Application of PCT International Application PCT/JP2010/000384.

TECHNICAL FIELD

The present invention relates to an electric discharge tube used as an artificial light source for photography or the like, a method for forming a reflective film of an electric discharge tube, and a light emitting device.

BACKGROUND ART

In recent years, a compact camera and a cellular phone with camera function are required to be miniaturized. Accordingly, an electric flash device used as an artificial light source is also required to be miniaturized.

A structure needs to be simplified to cope with miniaturization. In order to simplify a structure of a light-emitting unit of an electric flash device in which a reflective umbrella used in a conventional electric flash unit is eliminated and a reflective film is formed on an outer peripheral surface of an electric discharge tube is proposed (see Patent Document 1).

Figure 10:
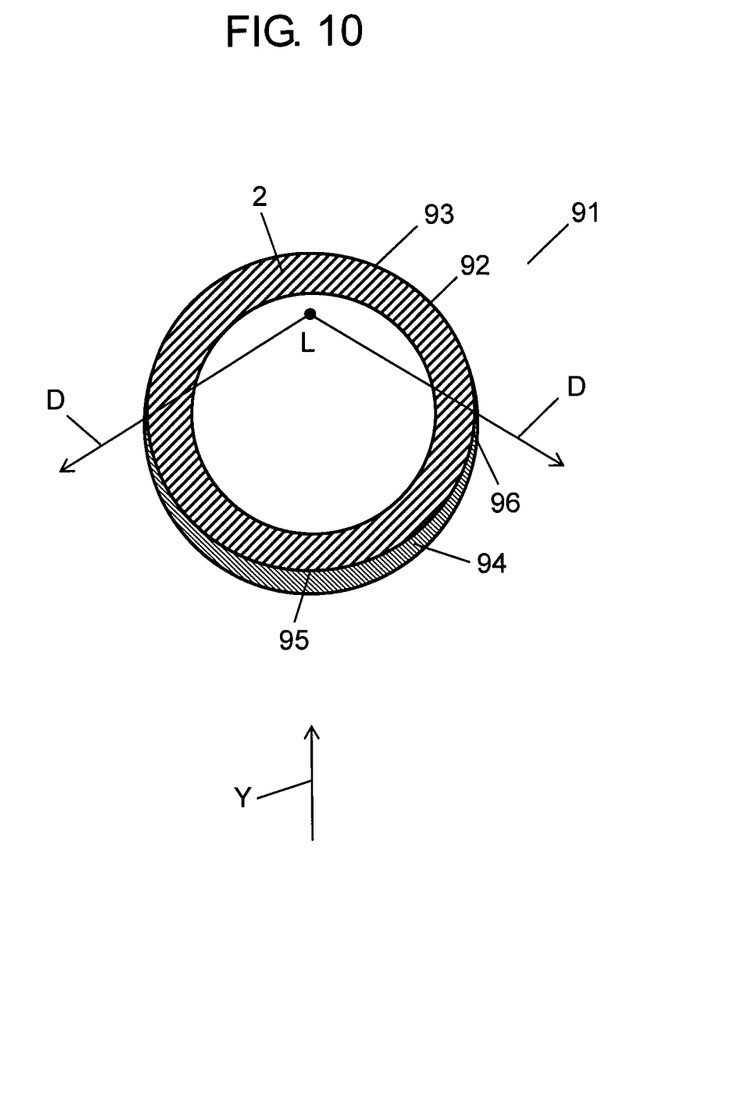
FIG. 10 is a sectional view showing an electric discharge tube in which a conventional reflective film is formed.

FIG. 10 is a sectional view showing an electric discharge tube used in a conventional electric flash device. In the electric flash device, reflective film 94 is formed on an outer peripheral surface of cylindrical glass bulb 92 serving as a constituent element of electric discharge tube 91 except for a belt-like (in FIG. 10, in a direction from the front surface of the plane of the drawing to the rear surface thereof) transparent portion 93 that transmits light. Reflective film 94 is formed by depositing a metal such as aluminum, silver or the like, and functions as a reflective umbrella that reflects light emitted in electric discharge tube 91.

However, since light emission in electric discharge tube 91 occurs by light emission of an entire gas excited in electric discharge tube 91, as shown in FIG. 10, light is not reflected by reflective film 94 at point L, and, as indicated by arrow D, the light is irradiated behind electric discharge tube 91 in vain. In order to reduce the light volume loss and to reflect light ahead of electric discharge tube 91, reflective film 94 formed in electric discharge tube 91 needs to be formed at a deposition angle of 180° or more in a circumferential direction on an outer peripheral surface in a more proper range to have a sufficient thickness.

When a reflective film obtained by metal deposition is to be formed by a conventional depositing method on an outer peripheral surface of cylindrical electric discharge tube 91 in a direction indicated by arrow Y, a deposition material easily adheres to outer peripheral surface 95 facing a deposition source. However, a deposition material does not easily adhere to outer peripheral surface 96 (semi-peripheral surface being far from the deposition source on a tube surface) that is hidden behind the deposition source, and reflective film 96 becomes extremely thin. For this reason, light emitted in electric discharge tube 91 cannot be sufficiently reflected.

However, a light emitting device such as an electric flash (strobe) device using a conventional electric discharge tube cannot obtain a uniform light intensity distribution because a light value is short.

PRIOR ART DOCUMENT

Patent Document

[Patent Document 1] Japanese Unexamined Patent Publication No. 7-72535

DISCLOSURE OF THE INVENTION

The present invention is to provide an electric discharge tube the light volume loss of which is reduced, a method for forming a reflective film of an electric discharge tube that can obtain a sufficient film thickness in a wide region of an outer peripheral surface, and a light emitting device that can obtain a uniform light intensity distribution.

The electric discharge tube according to the present invention includes a glass bulb and a reflective film formed in a region having an angle of at least 230° on the outer peripheral surface of the glass bulb. According to the configuration, since light emitted in the electric discharge tube is reflected in an irradiation direction without being irradiated behind the electric discharge tube, a light volume loss of the electric discharge tube can be reduced.

The method of forming a reflective film of an electric discharge tube according to the present invention has a configuration in which a reflective film on an outer surface of a glass bulb by depositing a metal from a deposition source from at least two directions. With the configuration, a sufficient film thickness can be obtained in a wide region of the outer peripheral surface of the electric discharge tube.

The light emitting device according to the present invention includes the electric discharge tube described above. With the configuration, since light emitted in the electric discharge tube has no component irradiated by a reflective film behind the electric discharge tube, a uniform light intensity distribution can be obtained. Therefore, a compact higher-efficient light emitting device can be obtained.

PREFERRED EMBODIMENTS FOR CARRYING OUT OF THE INVENTION

Figure 1:
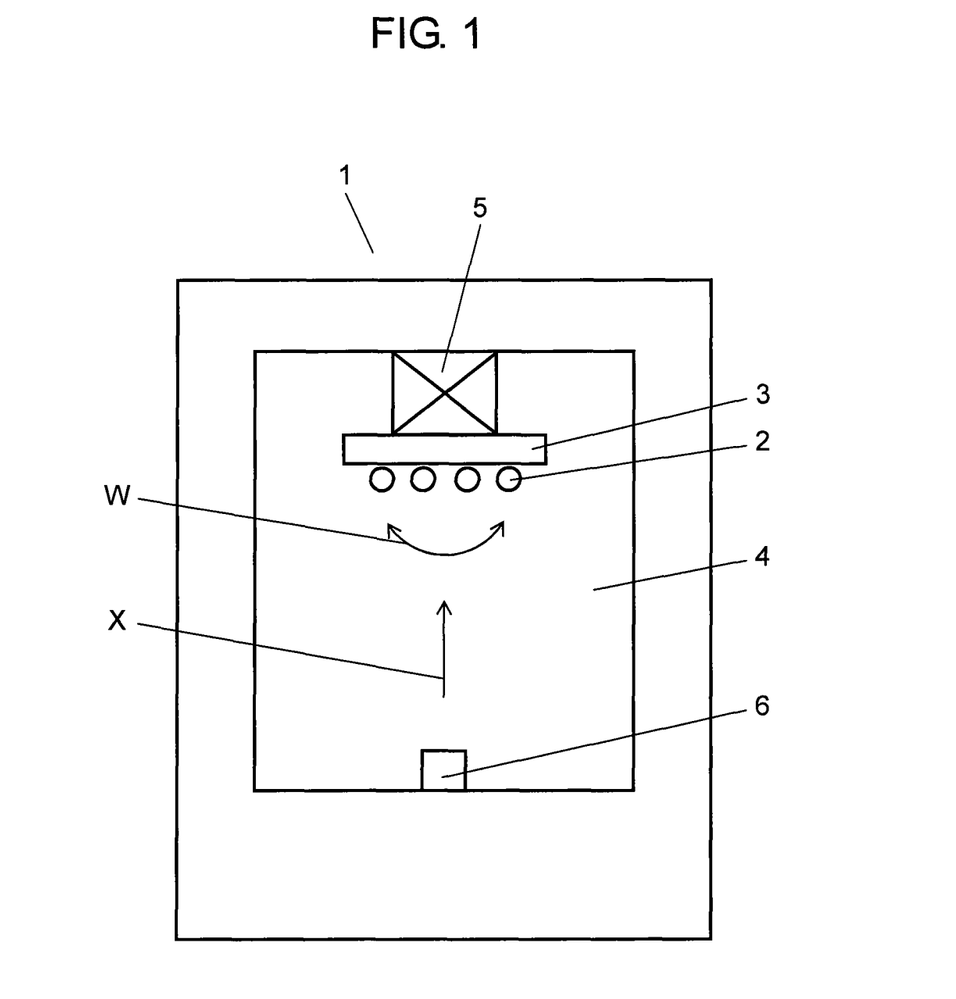
FIG. 1 is a schematic diagram of a vacuum deposition apparatus used in the method of forming a reflective film of an electric discharge tube according to an embodiment of the present invention.
Figure 2:
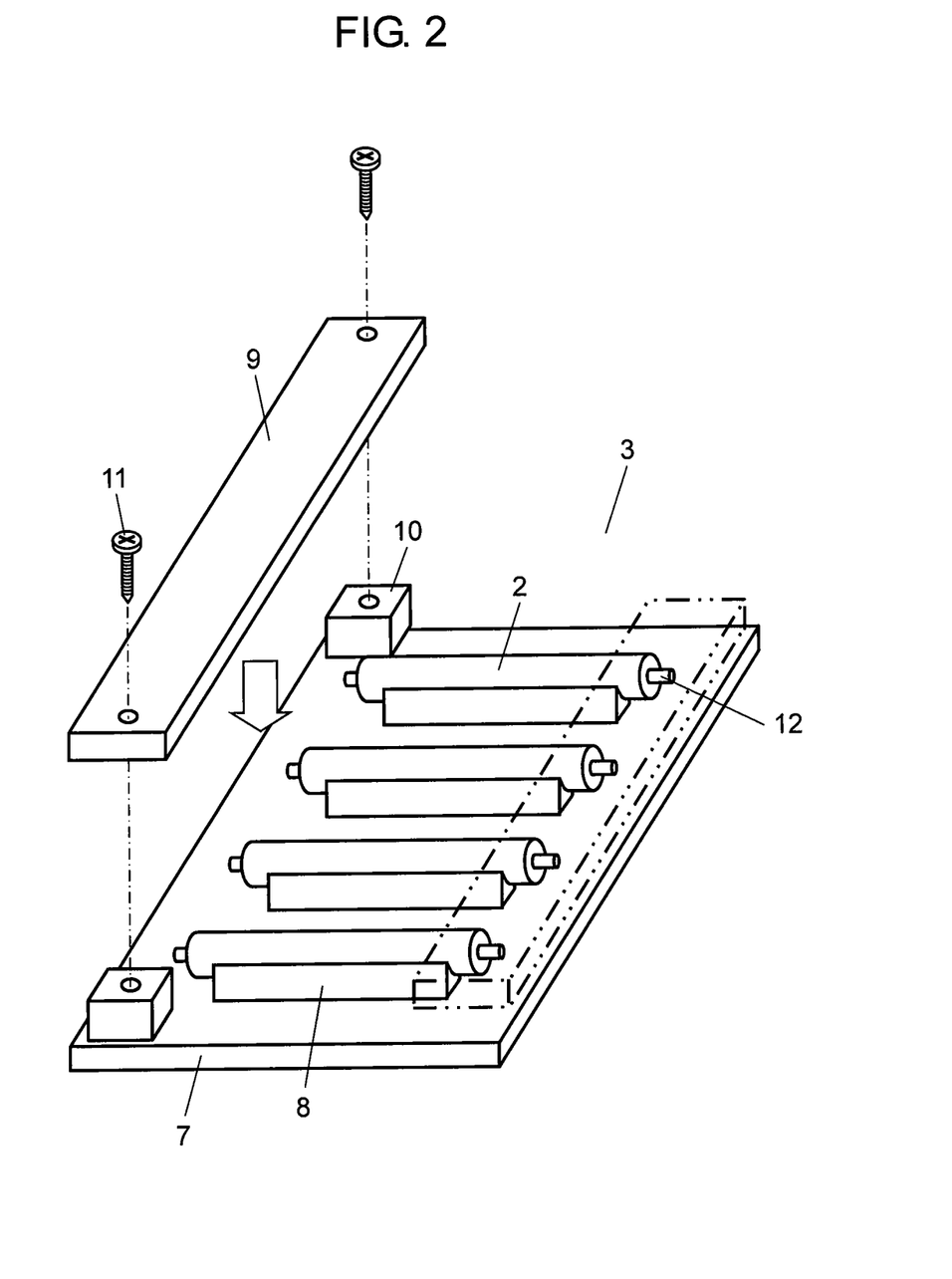
FIG. 2 is a perspective diagram showing a deposition jig used in the method of forming a reflective film of an electric discharge tube according to the embodiment.

The present invention will be described on the basis of an embodiment with reference to the accompanying drawings. FIG. 1 is a schematic diagram of a vacuum deposition apparatus used in the method of forming a reflective film of an electric discharge tube according to an embodiment of the present invention. FIG. 2 is a perspective diagram showing a deposition jig used in the method of forming a reflective film of an electric discharge tube according to the embodiment.

An outline of a method of forming a reflective film of an electric discharge tube by vacuum deposition will be described first. In FIG. 1, glass bulb 2 is fixed to deposition jig 3 and arranged in vacuum chamber 4 of vacuum deposition apparatus 1. On an outer peripheral surface of glass bulb 2, a reflective film is formed by depositing a metal from deposition source 6. Deposition jig 3 is designed to make it possible to set a plurality of glass bulbs 2 therein in terms of productivity. Deposition jig 3 is attached to tilting stage 5 on the upper side in vacuum chamber 4. Tilting stage 5 sets a rotating angle to tilt deposition jig 3 in a direction indicated by arrow W.

On the other hand, on a lower side in vacuum chamber 4, deposition source 6 formed by a metal material deposited on glass bulb 2 to serve as a reflective film is formed. As deposition source 6, a metal material such as aluminum, silver or the like is used. After glass bulb 2 and deposition source 6 serving as targets for deposition are arranged, vacuum chamber 4 is set in a vacuum state, and deposition source 6 is heated to evaporate the metal material in a direction indicated by arrow X. In this manner, a reflective film is formed on glass bulb 2.

A method of fixing glass bulb 2 to deposition jig 3 and a method of arranging deposition jig 3 in vacuum chamber 4 will be described below. Deposition jig 3, as shown in FIG. 2, is designed such that a plurality of masking jigs 8 are arranged on base plate 7. Each of masking jigs 8 is placed together with glass bulb 2 serving as a deposition target along longitudinal directions thereof. After glass bulb 2 is placed on each of masking jigs 8, portions near both cylindrical end portions of each of glass bulb 2 are fixed by pressing plate 9. Pressing plate 9 is fixed to attaching portion 10 on base plate 7 with screw 11 such that pressing plate 9 is brought into contact with both the end portions of each of glass bulbs 2.

After all masking jigs 8 and glass bulbs 2 are fixed on base plate 7, deposition jig 3 is arranged in vacuum chamber 4 of vacuum deposition apparatus 1 in a vertically inverted state (glass bulbs 2 are located under masking jigs 8). Although deposition jig 3, as described above, is attached to tilting stage 5 in vacuum chamber 4, deposition jig 3 is attached such that a rotating direction of tilting stage 5 is orthogonal to the longitudinal direction of glass bulb 2. More specifically, when a rotating angle of tilting stage 5 changes, an angle between deposition source 6 and outer periphery of glass bulb 2 changes in the circumferential direction of the glass bulb 2. Therefore, when tilting stage 5 is rotated to change relative positions of glass bulb 2 and deposition source 6, a metal material is deposited from deposition source 6 onto the outer surface of glass bulb 2 to make it possible to a reflective film.

Masking jig 8 is used to form a portion in the reflective film is not formed on the outer peripheral surface of glass bulb 2, i.e., a portion serving as a belt-like transparent portion that transmits light. Pressing plate 9 plays a role to fix masking jigs 8 and glass bulb 2 to each other and also plays a role to prevent a film from being formed on electrode 12 at both the ends of glass bulb 2 and glass portions of both the end portions.

Figure 3A:
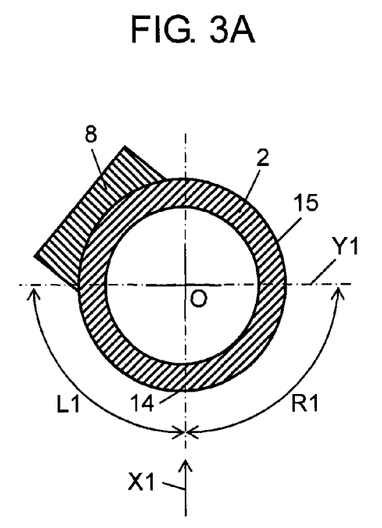
FIG. 3A is a sectional view of the electric discharge tube to explain the method of forming a reflective film of an electric discharge tube according to the embodiment.
Figure 3B:
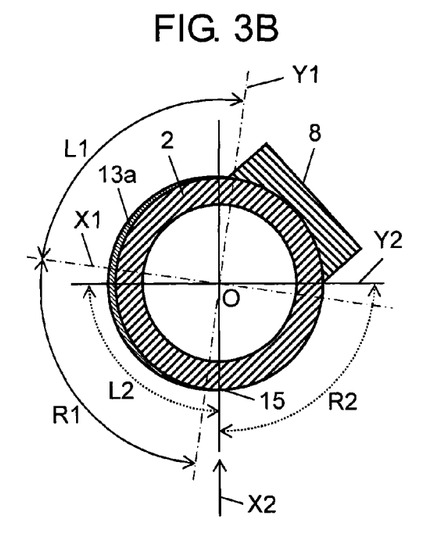
FIG. 3B is another sectional view of the electric discharge tube to explain the method of forming a reflective film of an electric discharge tube according to the embodiment.
Figure 3C:
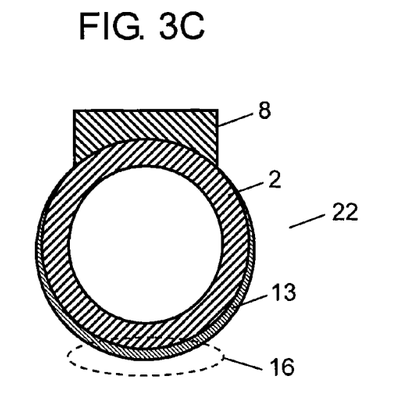
FIG. 3C is still another sectional view of the electric discharge tube to explain the method of forming a reflective film of an electric discharge tube according to the embodiment.

FIGS. 3A and 3B are sectional views of an electric discharge tube showing relative positions of deposition source 6 and glass bulb 2 when an angle between deposition source 6 and the outer periphery of glass bulb 2 is changed in the circumferential direction of glass bulb 2 by changing a rotating angle of tilting stage 5 to perform deposition twice. FIG. 3C is a sectional view of an electric discharge tube in which a reflective film is formed by performing deposition twice. As described above, deposition jig 3 on masking jigs 8 and glass bulb 2 are fixed is arranged in vacuum chamber 4, and vacuum chamber 4 is evacuated. After that, deposition source 6 is heated to evaporate a metal material, thereby forming reflective film 13 on glass bulb 2.

In a first step, a rotating angle of tilting stage 5 is set, and as shown in FIG. 3A, deposition is performed to glass bulb 2 in a direction indicated by arrow X1. Since a metal material does not adhere to a portion hidden by masking jig 8, reflective film 13 is not formed on the portion.

A line that is parallel to arrow X1 and passes through center point O of glass bulb 2 is defined as axis X1, and a line that is orthogonal to axis X1 and passes through center point O is defined as axis Y1. In this case, since region R1 extending from axis X1 (0°) to axis Y1 (right 90°) and region L extending from axis X1 (0°) to axis Y1 (left 90°) face deposition source 6, a metal material easily adhere to the regions, and reflective film 13 is formed to have a thickness that gradually decreases from axis X1 to axis Y1.

Since outer peripheral portion 15 (portion having an angle equal to or larger than left and right 90° of axis X1, i.e., a semi-peripheral surface over axis Y1) not facing deposition source 6 is hidden from deposition source 6, a metal material rarely adhere to the portion. For this reason, reflective film 13 cannot be formed to have a necessary film thickness.

In a second step, a rotating angle (for example, an angle over 90°) of tilting stage 5 is changed, as shown in FIG. 3B, deposition is performed to glass bulb 2 in a direction indicated by arrow X2. FIG. 3B shows that reflective film 13a deposited in the first step is formed from region R1 to region L1.

In the second step, a film is not formed on a portion hidden by masking jig 8. A line that is parallel to arrow X2 and passes through center point O of glass bulb 2 is defined as axis X2, and a line that is orthogonal to axis X2 and passes through center point O is defined as axis Y2. In this case, a metal film easily adhere to regions L2 and R2 facing deposition source 6.

Therefore, reflective film 13 is formed to have a thickness that gradually decreases from axis X2 to axis Y2. This is the same as that in deposition in the direction indicated by arrow X1.

Since region L1 that is deposited first crosses over axis Y2 with rotation of deposition jig 3 and is hidden from deposition material 6, a metal material does not easily adhere to the region. However, since region R1 is located to almost overlap region L2, region R1 faces deposition source 6, the metal material adheres to region R1 again to form reflective film 13. As a result, overlap region 16 (FIG. 3C) is formed.

Since outer peripheral portion 15 hidden from deposition source 6 in deposition in the direction indicated by arrow X1 is also located in region R2 facing deposition source 6, a metal material adheres to outer peripheral portion 15 to form reflective film 13.

Since deposition by sputtering does not have strong directivity in an injection region, as in the embodiment, deposition goes around to the periphery of the glass bulb by only rotating tilting stage 5. More specifically, even though deposition is not performed by rotating glass bulbs 2, reflective films 13 shown in FIG. 3C can be simultaneously formed on plurality of glass bulbs 2. Therefore, the apparatus is not complicated, and cost can be kept low.

When the above procedure is performed at least twice, depending on a necessary film thickness, a plurality of times, a metal material adheres to an entire outer peripheral surface that is not covered with masking jigs 8 of glass bulb 2. More specifically, even though a deposition angle of reflective film 13 exceeds 180°, electric discharge tube 22 shown in FIG. 3C in which reflective film 13 is formed to have a film thickness at which light is not transmitted.

At this time, deposition regions R1 and L2 face deposition source 6 times the number of which is larger than that of deposition regions L1 and R2. For this reason, deposition film 13, as shown in FIG. 3C, is formed to have a maximum thickness on overlapping portion 16 and a thickness that gradually decreases toward opening 18.

Figure 4A:
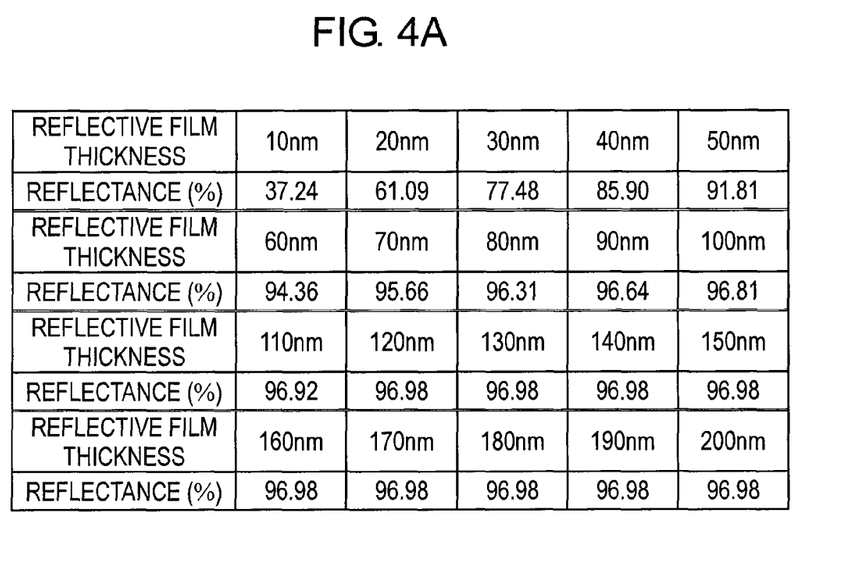
FIG. 4A is a diagram showing a relationship between a reflectance and a film thickness of a reflective film in the electric discharge tube according to the embodiment.
Figure 4B:
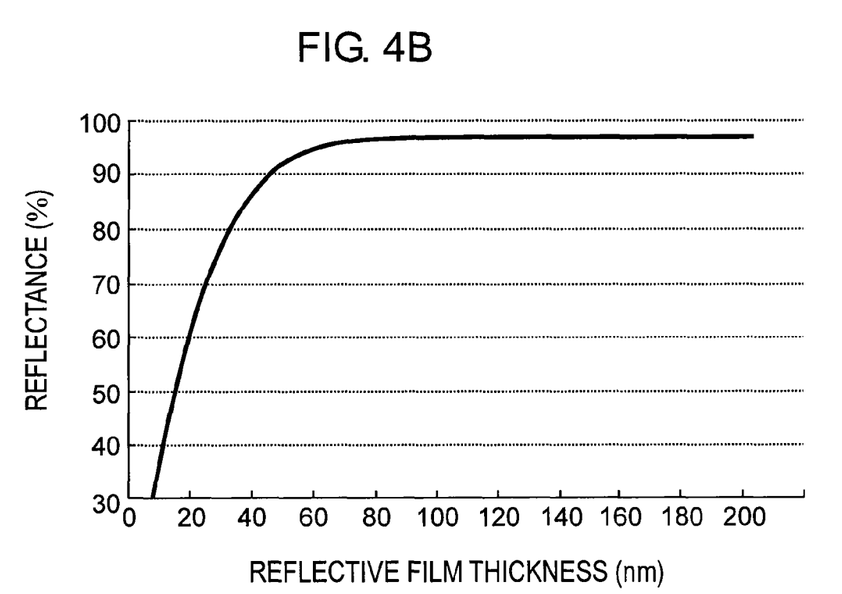
FIG. 4B is a graph showing a relationship between a reflectance and a film thickness of a reflective film in the electric discharge tube according to the embodiment.

FIGS. 4A and 4B are a diagram and a graph showing a relationship between a reflectance of reflective film 13 formed on electric discharge tube 22 and a thickness of reflective film 13. In FIGS. 4A and 4B, reflective film 13 is formed by using silver as deposition source 6, and an average value obtained when spectral reflectances in a band having emission wavelengths of 400 to 700 nm is shown.

On the basis of the result, deposition is performed such that the thickness of reflective film 13 is at least 50 nm or more and, preferably, 100 nm or more. When the thickness of reflective film 13 is 50 nm or more, a reflectance of 92% of a reflective umbrella used in a conventional electric flash device can be almost achieved, and light emitted in electric discharge tube 22 can be sufficiently reflected.

An opening of reflective film 13 that is easily peeled is formed to have a film thickness of 50 nm or more at which a reflectance is not deteriorated. On the other hand, a reflective film on a portion behind the reflecting tube in which metal particles may be scattered by impact or heat in emission of the electric discharge tube is preferably formed to have a film thickness of 100 nm or more to prevent a reflected light volume from decreasing.

When the entire area of reflective film 13 is desired to have a reflectance higher than that of a conventional reflective umbrella, the film is preferably formed to have a film thickness of at least 80 nm or more. The reflective film thickness on the portion behind electric discharge tube 22 is a film thickness of 100 nm or more by the depositing method. However, since the reflectances at the film thicknesses of 100 to 200 are almost equal to each other, high reflectances of almost 96% can be averaged in the entire region of reflective film 13 to effectively suppress a light distribution from being uneven.

A region (portion covered with masking jig 8) in which reflective film 13 is not formed serves as opening 18 (transparent portion) in electric discharge tube 22. When electric discharge tube 22 is built in as an electric flash device, light emitted in the electric discharge tube includes a component irradiated backward when an angle (angle of aperture) in the circumferential direction of opening 18 of electric discharge tube 22 when viewed from the front is a predetermined value or less. More specifically, when opening 18 is not located ahead of the end portion of reflective film 13 when viewing electric discharge tube 22 incorporated as the electric flash device in front, the light emitted in the electric discharge tube includes a component irradiated backward. Therefore, the component irradiated backward becomes a light volume loss. In this case, when an angle of aperture, an outer radius of electric discharge tube 22, and an internal radius of electric discharge tube 22 are represented by $2\theta$, Ro, and Ri, respectively, a relationship given by $\cos\theta = Ri/Ro$ is satisfied. Therefore, in accordance with a ratio of outer radius Ro and internal radius Ri of electric discharge tube 22, $\theta$ needs to be set to a predetermined value or less. On the basis of a size of a generally manufactured flash electric discharge tube having a small diameter, an example of a deposition angle of reflective film 13 is shown in FIG. 5A.

Figure 5A:
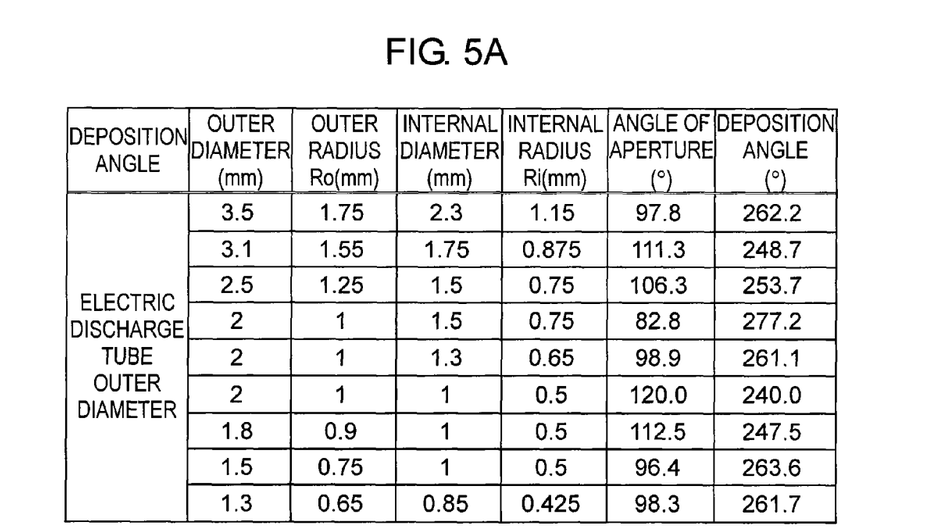
FIG. 5A is a diagram showing a relationship between a size of the electric discharge tube and a deposition angle of a reflective film according to the embodiment.

In FIG. 5A, for example, when an outer diameter, an outer radius, and an internal radius are given by 1.3 mm, Ro=0.65 (mm), and Ri=0.425 (mm), respectively, $2\theta$=98.3 is satisfied. For this reason, an angle of aperture needs to be set to the value or less. More specifically, a region in which a reflective film is formed needs to have an angle of 360°−98.3°=261.7° or more.

In consideration of relationships between outer diameters and internal diameters of various electric discharge tubes 22 that are practically used and a manufacturing error (common difference of parts) of electric discharge tube 22 or the like, a region in which the reflective film is formed preferably has at least an angle of 240°.

Since reflective film 13 is not formed on a portion hidden by masking jig 8, reflective film can be formed in an appropriate region that requires reflective film 13.

In recent years, electric flash devices having various sizes such as an electric flash device for a compact camera and a large-size electric flash device are present. For this reason, electric discharge tubes 22 having various sizes are required. For this reason, examples of deposition angles of reflective film 13, when the outer diameter of glass bulb 2 is narrowed to miniaturize a flash electric discharge tube and when the outer diameter of glass bulb 2 is increased in size to increase a capacity of an enclosed gas to obtain a large amount of light emission are shown in FIG. 5B.

Figure 5B:
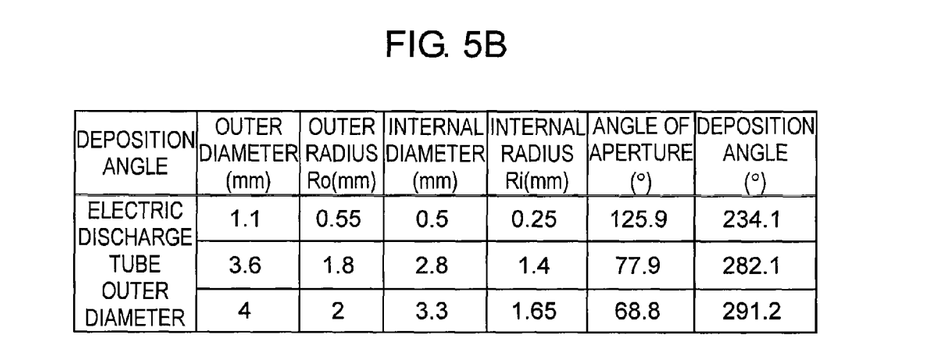
FIG. 5B is a diagram showing another relationship between a size of the electric discharge tube and the deposition angle of the reflective film according to the embodiment.

In FIG. 5B, for example, in an electric discharge tube for a compact electric flash having an outer diameter of 1.1 mm, an outer radius Ro=0.55 (mm), and an internal radius Ri=0.25 (mm), $2\theta$=125.9° is satisfied. For this reason, an angle of aperture needs to be set to the value or less. More specifically, a region in which a reflective film is formed needs to have an angle of about 360°−125.9°=234.1°.

In consideration of a relationship between an outer diameter and an internal diameter of compact electric discharge tubes 22 that are practically used and a manufacturing error (common difference of parts) of electric discharge tube 22 or the like, a region in which the reflective film is formed preferably has at least an angle of about 230°.

In an electric discharge tube for a large-size electric flash having an outer diameter of 4.0 mm, an outer radius Ro=2.0

(mm), and an internal radius Ri=1.65 (mm), 2θ=68.8° is satisfied. For this reason, an angle of aperture needs to be set to the value or less. More specifically, a region in which a reflective film is formed needs to have an angle of about 360°−68.8°=291.2°.

In consideration of a relationship between an outer diameter and an internal diameter of large-size electric discharge tube 22 that is practically used and a manufacturing error (common difference of parts) of electric discharge tube 22 or the like, a region in which the reflective film is formed preferably has at least an angle of about 290°.

As described above, by the method of forming a reflective film according to the embodiment, relative angle positions of electric discharge tube 22 and deposition source 6 around an axis of electric discharge tube 22 are changed to form a film at least an angle of 230°. In this case, light volume losses of practically used electric discharge tubes 22 having various sizes can be minimized.

Figure 6A:
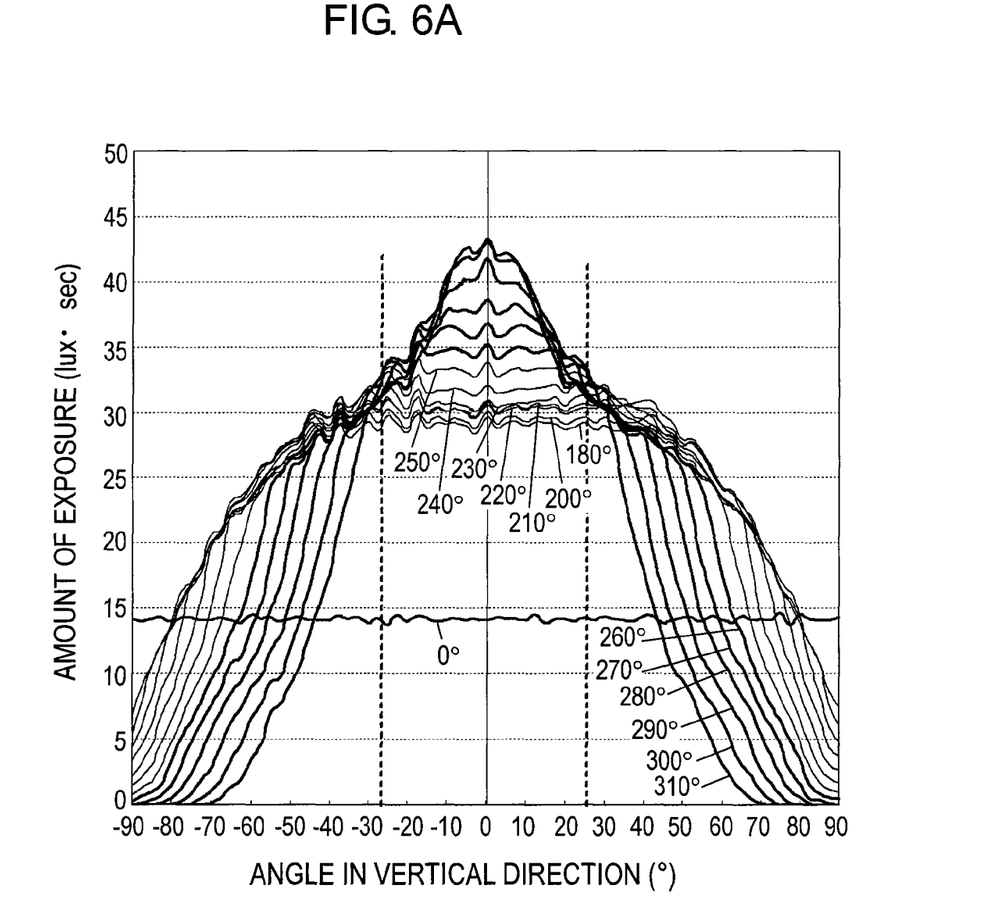
FIG. 6A is a graph showing a relationship between a light-emitting direction and a light volume in the electric discharge tube according to the embodiment.
Figure 6B:
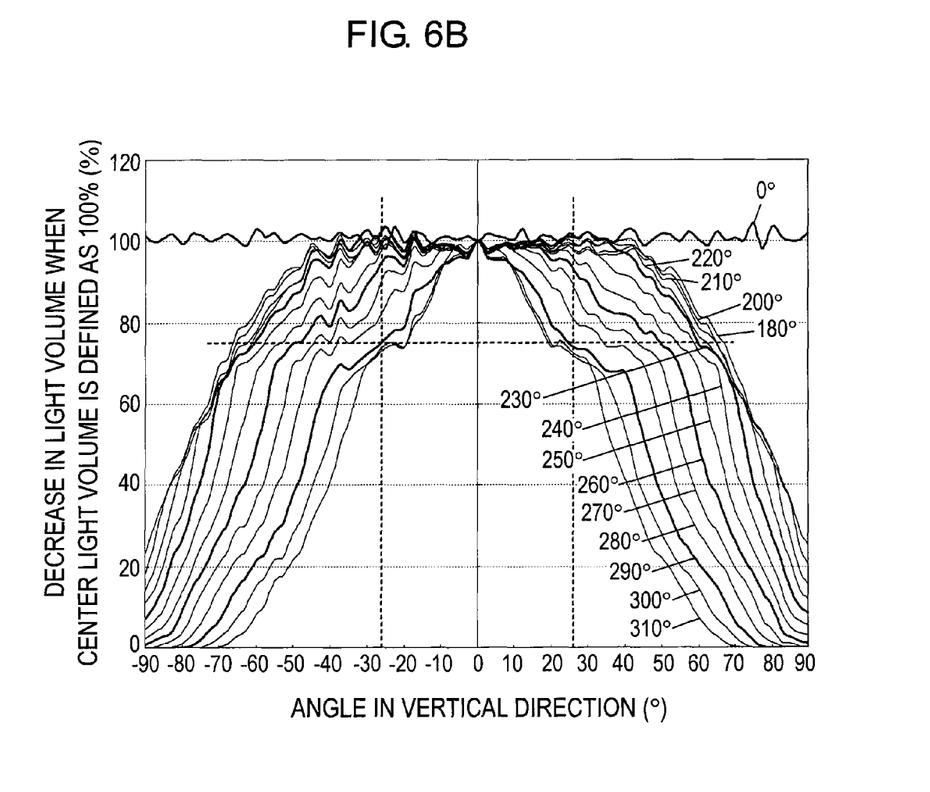
FIG. 6B is another graph showing a relationship between a light-emitting direction and a light volume in the electric discharge tube according to the embodiment.

When electric discharge tube 22 is used in an electric flash device, electric discharge tube 22 needs to be designed to reduce a loss of beam and reduce uneven irradiation in a desired irradiation region. FIG. 6A is a graph showing a relationship between a light volume and a light irradiation direction of electric discharge tube 22 according to the embodiment, and shows light volumes in vertical directions, i.e., energy amounts in required angles in units of deposition angles of a deposition film. FIG. 6B is a graph showing a relationship between an attenuation and a light irradiation direction of electric discharge tube 22 according to the embodiment, and shows attenuations ratio in required angles in units of deposition angles of a deposition film with reference to vertically distributed lights, i.e., a central light volume. Numbers (0°, 180° . . . 310°) on characteristic curves shown in the drawings denote deposition angles of a deposition film, respectively. In the embodiment, when electric discharge tube 22 is used as an electric flash device, electric discharge tube 22 is used to have a horizontal light axis.

In FIGS. 6A and 6B, in a required specification of an electric flash device, in terms of a 35-mm lens, an angle of field of a 28-mm focal length is set. In order to suitable for the specification, the vertical irradiation angles of electric discharge tube 22 were set to 27° each with respect to a light axis, i.e., a total of about 54°. In this state, electric discharge tube 22 in which reflective film 13 is formed on glass bulb 2 having an outer diameter of 1.3 mm and an internal diameter of 0.85 mm at deposition angles of 180° to 310° (angles of aperture of reflective film 13 are 50° to 180°) and electric discharge tube 22 in which reflective film 13 is not formed were used to emit light. An input voltage to electric discharge tube 22 was set to 320 V, and a main capacitor capacitance was set to 75 μF. In light emission, only electric discharge tube 22 is used to emit light without using an optical panel. When the opening is excessively small, light excessively converges on the center. In a light-emitting tube using a glass bulb, light distribution cannot be simply designed by only a light source. For this reason, since the light source is preferably combined to a reflective umbrella or a panel, light is conveniently leaks outside a region having an angle of 54°. In the region having the angle of 54°, flat light distribution that is free from a large peak if possible is preferable.

As is apparent from FIG. 6A, since electric discharge tube 22 in which reflective film 13 is not deposited (deposition angle of 0°) irradiates light in all the directions about electric discharge tube 22, a large number of beam are irradiated outside an irradiation region.

At deposition angles of 180° to 220°, amounts of exposure in regions up to 27° in vertical directions approximate to about 30 lux·sec. When the deposition angle is 230° or more, a light volume at a center portion increases by about 2 lux·sec each time the deposition angle increases by 10° (opening narrows by 10°). For this reason, by an angle of aperture is reduced, a loss of beam irradiated outside the irradiation region can be reduced.

On the other hand, in consideration of a light distribution balance in the vertical directions, in order to suppress uneven irradiation, when a light volume at the center portion is considered as 100%, decreases in light volume at angles of about 27° in the vertical (up and down) directions need to be about 25% or less. As shown in FIG. 6B, when a reflective film is deposited at an angle of 300° or more, a beam is irradiated on only a center portion because the opening is narrow. Therefore, decreases in light volume at portions at angles of 18° or more in the vertical directions are 25% or more, uneven irradiation occurs. When the reflective film is deposited at an angle of 290° or less, decreases in light volume at angles of about respective 27° in up and down directions can be about 25% or less.

In this manner, the opening needs to be narrowed to reduce a light volume loss, and the opening needs to be widened to reduce uneven irradiation. For this reason, in order to satisfy both the reductions in light volume loss and uneven irradiation, a range of deposition angles of about 230° to 290° is an optimum range.

The range of the deposition angles may be set on the basis of the above equation by using an outer diameter and an internal diameter of electric discharge tube 22 to be used.

In the embodiment, on the basis of the above equation, the deposition angle is set to about 260°. At this time, as is apparent from FIGS. 6A and 6B, amounts of exposure are 35 lux·sec at up to angles of about respective 17° in up and down directions. With respect to light distribution, decreases in light volume are suppressed to about 10% even at angles of about respective 27° in up and down directions. More specifically, both a reduction in light volume loss and suppression of uneven irradiation can be satisfied.

After reflective film 13 is deposited, a protective film (not shown) may be formed. The protective film is formed such that a metal such as tin or indium is sprayed on an outer peripheral surface of electric discharge tube 22 in which reflective film 13 is formed and that is put in a furnace heated to 500 to 700° C. The metal such as tin or indium is used as a transparent conductive film (NESA film) in a general flash electric discharge tube. For this reason, when the film is formed on the outer peripheral surface of electric discharge tube 22 in which reflective film 13 is formed, light from electric discharge tube 22 can be transmitted. In addition, since a transparent crystalline layer is obtained by spraying a metal in a heated furnace, the film is suitable for a protective film for reflective film 13.

When silver is used as reflective film 13, the silver is easily blackened by atmospheric oxygen, a sulfur content, or the like. However, the protective film is formed to prevent reflective film 13 from being deteriorated and to make it possible to prevent reflective film 13 from being peeled from opening 18.

Figure 7:
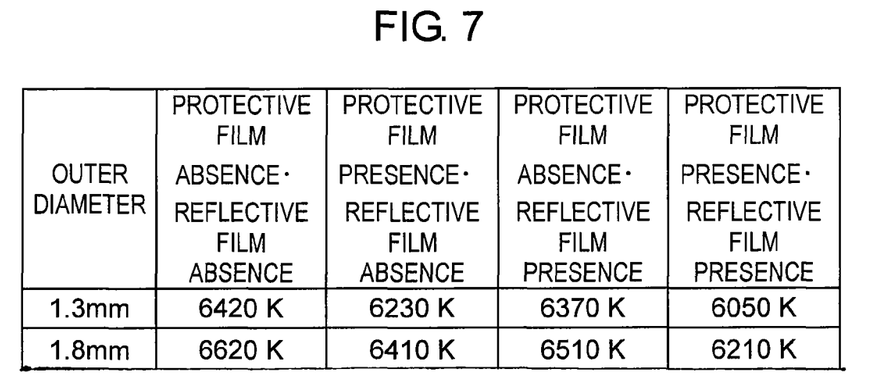
FIG. 7 is a diagram showing comparison of color temperatures in light emission of the electric discharge tube according to the embodiment.

Light emitted from electric discharge tube 22 transmits a metal thin film to make it possible to decrease a color temperature. FIG. 7 shows comparison of color temperatures in light emission of a general electric discharge tube and the electric discharge tube according to the embodiment.

FIG. 7 shows results obtained such that a protective film configured by transparent conductive films and reflective film 13 are formed by the following combinations of 4 types by using electric discharge tubes 22 of two types having outer diameters of 1.3 mm and 1.8 mm and connected to a circuit having an input voltage of 320 V and a main capacitor of 75-μF to measure color temperatures in light emission.

(1) Absence of protective film·Absence of reflective film 13
(2) Presence of protective film·Absence of reflective film 13
(3) Absence of protective film·Presence of reflective film 13
(4) Presence of protective film·Presence of reflective film 13

As shown in FIG. 7, in comparison with electric discharge tube 22 in which a protective film is absent and a reflective film is absent, in electric discharge tube 22 in which the protective film is present and the reflective film is present, a color temperature decreases by about 400 to 600 K. In comparison with electric discharge tube 22 in which the protective film is absent and the reflective film is present, a color temperature decreases by about 200 K.

When electric discharge tube 22 is used in an electric flash device, an optical panel of the electric flash device may be clouded by light from electric discharge tube 22. However, the color temperature of electric discharge tube 22 is decreased by using the protective film according to the present invention, and the optical panel can be suppressed from being deteriorated, for example, clouded.

An electric flash device according to the embodiment using, as a light-emitting unit, electric discharge tube 22 in which the reflective film is formed as described above is formed will be described below. Since a region in which reflective film 13 is formed is set to at least 230° in electric discharge tube 22 described above, light emitted in electric discharge tube 22 does not include a component irradiated backward, and a high-efficiency electric flash device having a small light volume loss can be obtained.

Figure 8:
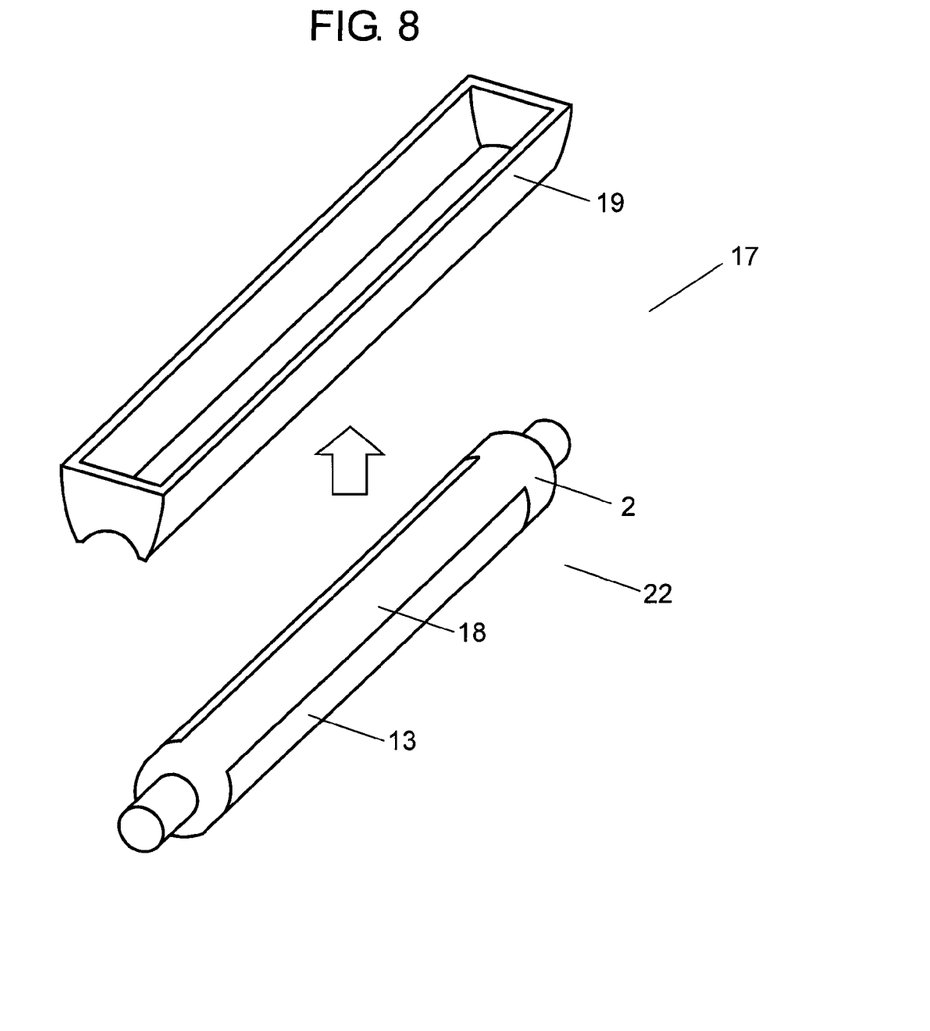
FIG. 8 is an exploded diagram of a main part of an electric flash unit according to the embodiment.
Figure 9A:
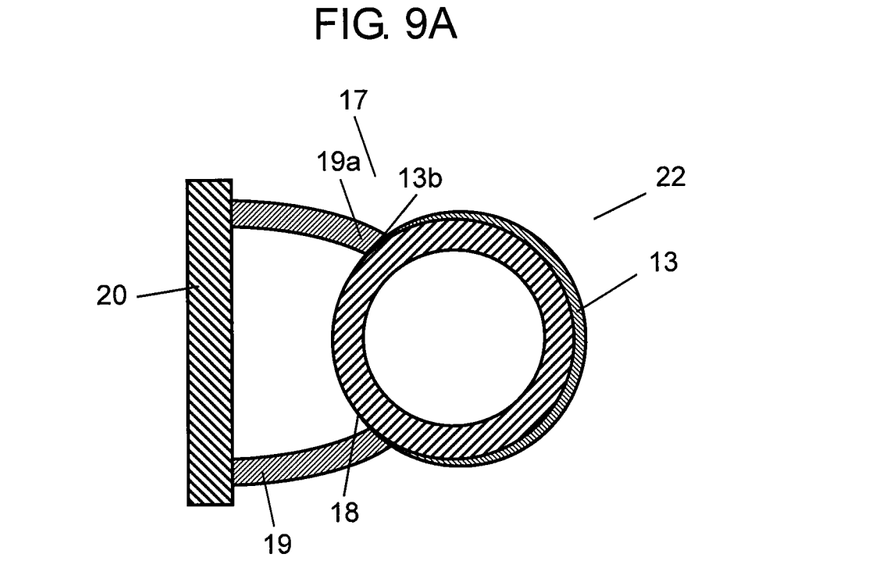
FIG. 9A is a sectional view showing an example of an electric flash unit according to the embodiment.

FIG. 8 is an exploded diagram of an electric flash unit obtained by combining electric discharge tube 22 and reflecting member 19. FIG. 9A is a sectional view showing an example of electric flash unit 17 using electric discharge tube 22 having reflective film 13 as a light-emitting unit. Reflecting member 19 is brought into tight contact with electric discharge tube 22 shown in FIG. 9A, and transparent optical panel 20 is combined to electric discharge tube 22.

Reflective film 13 is formed in electric discharge tube 22, and reflective film 13 is deposited from the internal diameter edge portion of electric discharge tube 22 to the front side (toward reflecting member 19). For this reason, a reflective umbrella need not be formed in the back of irradiation of light. However, in order to improve light-emitting efficiency by focusing light irradiated from opening 18 and scattered forward, reflecting member 19 is used. Reflecting member 19 is formed such that opening 19a being in tight contact with electric discharge tube 22 overlaps end portion 13b of reflective film 13.

Electronic flash unit 17 configured by electric discharge tube 22 in which reflective film 13 is deposited and reflecting member 19 has no structure in which the reflective umbrella is arranged at the rear. Since electronic flash unit 17 can efficiently converge light by reflective film 13, a size in an optical axis direction can be decreased. For this reason, a compact electric flash device can be obtained.

A configuration in which reflecting member 19 overlaps end portion 13b of reflective film 13 is employed to prevent from being formed between opening 19a of reflecting member 19 and opening 18 of electric discharge tube 22. When the gap is formed between opening 19a of reflecting member 19 and opening 18 of electric discharge tube 22, flash light from electric discharge tube 22 leaks from the gap to cause a light volume loss. In the embodiment, since the gap is not formed, a light volume loss can be prevented. Flash light output from opening 18 of electric discharge tube 22 is reliably converged by reflecting member 19 and distributed by optical panel 20 to an irradiation region of electric flash light.

Figure 9B:
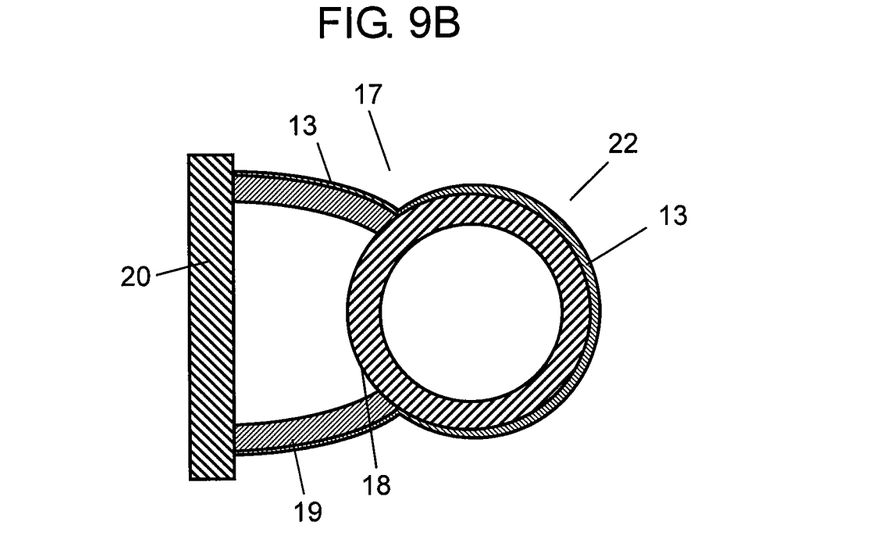
FIG. 9B is a sectional view showing another example of the electric flash unit according to the embodiment.

FIG. 9B is a sectional view showing an example of electronic flash unit 17 when, by using reflecting member 19 as a masking jig in deposition, a combination between electric discharge tube 22 and reflecting member 19 is fixed to a deposition jig to deposit reflective film 13. Unlike in FIG. 9A, reflecting member 19 does not overlap end portion 13b of reflective film 13. However, when deposition is performed by masking electric discharge tube 22 with reflecting member 19, reflective film 13 can be more easily formed at an appropriate deposition angle.

Since a gap portion between electric discharge tube 22 and reflecting member 19 is covered with a deposited metal material, a gap is not easily formed between electric discharge tube 22 and reflecting member 19. As in the configuration in FIG. 9A, flash light of electric discharge tube 22 does not form a gap between opening 19a of reflecting member 19 and opening 18 of electric discharge tube 22. For this reason, a high-efficiency electric flash device having a small light volume loss can be easily obtained.

The present invention is not limited to the above embodiment, and can be variously changed without departing from the spirit and scope of the invention as a matter of course.

For example, in the embodiment, tilting stage 5 is rotated to change an angle of the outer periphery of electric discharge tube 22 from deposition source 6. However, the invention is not limited to the configuration. For example, electric discharge tubes 22 may be independently rotated one by one. Deposition source 6 may be moved to change an angle with respect to the outer periphery of electric discharge tube 22.

In the embodiment, although a vacuum depositing method is employed as a depositing method, deposition may be performed by a sputtering method or an ion-plating method.

In the above embodiments, the electric discharge tube used in the electric flash device is described. However, in recent years, light-irradiation therapeutic apparatus that treats skin diseases by using a xenon lamp, an optical beauty apparatus that smoothens a rough skin by using the same xenon lamp, an optical epilation apparatus using a flash lamp, and the like and a therapeutic apparatus, a beauty apparatus, and the like using electric discharge tubes are developed. A light emitting device used in the therapeutic apparatus or a beauty apparatus needs to converge light emitted from the electric discharge tube toward a hide or a skin. Therefore, as in an electric discharge tube of the electric flash device according to the embodiment, in the light emitting device in a therapeutic apparatus, a beauty apparatus, or the like, by using an electric discharge tube in which a reflective film is formed in a region having an angle of at least 230° on the outer peripheral surface of a glass bulb, a light volume loss to a hide or a skin is reduced to make it possible to improve the effects of treatment and beautification.

As described above, the electric discharge tube according to the present invention includes a glass bulb and a reflective film formed in a region having an angle of at least 230° on the outer peripheral surface of the glass bulb. According to the configuration, since light emitted in the electric discharge tube is reflected in an irradiation direction without being irradiated behind the electric discharge tube, a light volume loss of the electric discharge tube can be reduced.

The electric discharge tube according to the present invention is formed such that the reflective film is formed in a region having an angle between 230° and 290° on the outer peripheral surface of the glass bulb. According to the configuration, both the reductions in light volume loss and uneven irradiation can be satisfied.

The electric discharge tube according to the present invention has a region in which the reflective film has an area formed into a thickness of at least 50 nm. According to the configuration, since the reflective film is deposited not to have an extremely small thickness, light emitted in the electric discharge tube is reflected without being transmitted through the reflective film and can be more reliably converged in a light axis direction of the electric discharge tube.

The electric discharge tube according to the present invention is formed such that the reflective film is formed in a manner to increase a film thickness toward a rear side from an opening where the reflective film is not formed. When the thickness of the metal deposition film increases, the film is easily peeled from the cylindrical electric discharge tube by increasing the metal characteristics (for example, elastic modules). On the other hand, when light emission from the electric discharge tube is repeated, metal particles are scattered by heat or impact, and the film is gradually decreases in thickness and then transmit light. For this reason, the film requires a predetermined film thickness or more to use the film as a reflective film. Therefore, in the electric discharge tube according to the present invention, since an opening of the reflective film that is easily peeled is formed to have a small thickness, the reflective film is not easily peeled. Since the film thickness of the reflective film on a rear portion of the electric discharge tube that reflects a large amount of light is large, a decrease in reflectance can be prevented even though metal particles are scattered.

In the electric discharge tube according to the present invention, a protective film is formed on a surface of the reflective film. According to the configuration, the protective film prevents the reflective film being deteriorated or peeled, and, at an opening portion of the reflective film, a color temperature of light transmitted through the protective film can be lowered.

In the electric discharge tube according to the present invention, the protective film is a metal thin film. According to the configuration, the metal thin film further prevents the reflective film being deteriorated or peeled, and, at an opening portion of the reflective film, a color temperature of light transmitted through the metal thin film can be further lowered.

Furthermore, the method of forming a reflective film of an electric discharge tube according to the present invention has a configuration in which a step of forming the reflective film on an outer surface of a glass bulb by depositing a metal from a deposition source from at least two directions. With the configuration, since deposition can be performed such that the metal material adheres at different angles, a sufficient film thickness can be obtained in a wide region having an angle of, for example, at least 230° on the outer peripheral surface of the electric discharge tube.

The method of forming a reflective film of an electric discharge tube according to the present invention includes a first step of forming the reflective film by depositing a metal from a deposition source on an outer surface of a glass bulb; and a second step of forming the reflective film by depositing a metal from the deposition source on the outer surface of the glass bulb after changing a relative position of the glass bulb with respect to the deposition source following the first step. With the configuration, since deposition can be performed such that the metal material adheres at different angles, a sufficient film thickness can be obtained in a wide region having an angle of, for example, at least 230° on the outer peripheral surface of the electric discharge tube.

The method of forming a reflective film of an electric discharge tube according to the present invention has a configuration in which a reflective film is formed in a region having an angle of at least 230° on the outer peripheral surface of the glass bulb. According to the configuration, since light emitted in the electric discharge tube is reflected in an irradiation direction without being irradiated behind the electric discharge tube, a light volume loss of the electric discharge tube can be reduced.

The method of forming a reflective film of an electric discharge tube according to the present invention has a configuration in which the deposition is performed by changing the relative position of the glass bulb and the deposition source along an outer circumferential direction of the glass bulb. With the configuration, a portion hidden from the discharge source is not formed on the outer peripheral surface of the glass bulb, and metal particles repeatedly adhere to a portion serving as an end portion of a deposition region in the previous deposition. For this reason, a necessary film thickness can be obtained even though a deposition angle of the reflective film is large.

The method of forming a reflective film of an electric discharge tube according to the present invention has a configuration in which the reflective film formed in the second step is deposited in a manner to overlap the reflective film formed in the first step. With the configuration, a necessary film thickness can be obtained even though a deposition angle of the reflective film is large.

The method of forming a reflective film of an electric discharge tube according to the present invention has a configuration in which the step of depositing the metal on the outer surface of the glass bulb includes use of a masking jig to provide a region where the metal is not deposited. With the configuration, since a metal material is not formed on a portion hidden by the masking jig, even though facing positions of the electric discharge tube and the deposition source are changed, the metal material is deposited in an appropriate region that requires the reflective film.

The method of forming a reflective film of an electric discharge tube according to the present invention has a configuration in which the masking jig comprises a reflecting member brought into tight contact with the outer peripheral surface in front of the glass bulb. With the configuration, the reflective film can be more easily formed at an appropriate deposition angle. Accordingly, since a gap portion between the electric discharge tube and the reflecting member is covered with a deposited metal material, the gap between the electric discharge tube and the reflecting member is eliminated, and a high-efficiency electric flash device having a small light volume loss can be easily obtained.

Furthermore, the light emitting device according to the present invention has a configuration in which the electric discharge tube used as a light-emitting unit. With the configuration, since light emitted in the electric discharge tube has no component irradiated by a reflective film behind the electric discharge tube, a compact higher-efficiency light emitting device can be obtained.

The light emitting device according to the present invention has a configuration in which a reflecting member is arranged in front of the electric discharge tube. With the configuration, since light-emitting efficiency is improved by focusing light irradiated forward and scattered, a higher-efficiency light emitting device can be obtained.

INDUSTRIAL APPLICABILITY

According to the present invention, a high-efficiency electric discharge tube having a small light volume loss can be obtained. For this reason, the present invention is effectively used in an electric flash device, a light emitting device for treatment or beautification, and the like.

REFERENCE MARKS IN THE DRAWINGS

1 Vacuum deposition apparatus
2 Glass bulb
3 Deposition jig
4 Vacuum chamber
5 Tilting stage
6 Deposition source
7 Base plate
8 Masking jig
9 Pressing plate
10 Attaching portion
11 Screw
12 Electrode
13, 13a Reflective film
13b End portion
14, 15 Outer peripheral surface
16 Overlapping portion
17 Electric flash unit
18, 19a Opening
19 Reflecting member
20 Optical panel
22 Electric discharge tube

The invention claimed is:

1. An electric discharge tube comprising a glass bulb and a reflective film formed in a region having an angle of at least 230° on an outer peripheral surface of the glass bulb, wherein the reflective film is formed in a manner to increase a film thickness toward a rear side from an opening where the reflective film is not formed.

2. The electric discharge tube of claim 1, further comprising a protective film comprised by a metal thin film is formed on a surface of the reflective film.

3. A light emitting device comprising the electric discharge tube according to claim 2 used as a light-emitting unit.

4. A light emitting device comprising the electric discharge tube according claim 1 used as a light-emitting unit.

5. The light emitting device according to claim 4, wherein a reflecting member is arranged in front of the electric discharge tube.

6. A method of forming a reflective film of an electric discharge tube comprising a step of forming the reflective film in a region on an outer surface of a glass bulb by depositing a metal from a deposition source from at least two directions,
wherein, when the metal is deposited on the outer surface of the glass bulb, a reflecting member is arranged on the glass bulb as a masking jig such that the reflecting member is brought into tight contact with the outer surface of the glass bulb, and upon removing the reflecting member, an opening in the reflective film is formed, and
wherein the reflective film is formed in a manner to increase a film thickness toward a rear side from the opening.

7. The method of forming a reflective film of an electric discharge tube according to claim 6, wherein the region has an angle of at least 230° on the outer surface of the glass bulb.

8. A method of forming a reflective film of an electric discharge tube comprising: forming a first reflective film by depositing a metal from a deposition source in a region on an outer surface of a glass bulb; and forming a second reflective film by depositing the metal from the deposition source in a region on the outer surface of the glass bulb,
wherein, when the metal is deposited on the outer surface of the glass bulb, a reflecting member is arranged on the glass bulb as a masking jig such that the reflecting member is brought into tight contact with the outer surface of the glass bulb, and upon removing the reflecting member, an opening in the reflective film is formed, and
wherein the first and second reflective films have a combined thickness that increases toward a rear side from the opening.

9. The method of forming a reflective film of an electric discharge tube according to claim 8, further comprising changing the relative position of the glass bulb and the deposition source along an outer circumferential direction of the glass bulb.

10. The method of forming a reflective film of an electric discharge tube according to claim 8, wherein the second reflective film is deposited in a manner to overlap the first reflective film.

11. The method of forming a reflective film of an electric discharge tube according to claim 8, wherein the region has an angle of at least 230° on the outer surface of the glass bulb.

* * * * *